United States Patent
Sale et al.

[19]

[11] Patent Number: 6,164,967
[45] Date of Patent: Dec. 26, 2000

[54] FLUID DELIVERY DENTAL CLEANING DEVICE

[75] Inventors: David William Sale, Heber Springs; Ronald W. Haynes, Shirley, both of Ark.

[73] Assignee: Professional Dental Technologies, Inc., Batesville, Ark.

[21] Appl. No.: 09/328,619

[22] Filed: Jun. 9, 1999

Related U.S. Application Data

[60] Provisional application No. 60/100,361, Sep. 15, 1998.

[51] Int. Cl.[7] ................................................... A61G 17/02
[52] U.S. Cl. ............................. 433/80; 433/89; 433/216; 15/22.1
[58] Field of Search ................................. 433/80, 81, 82, 433/87, 89, 216; 601/162, 164; 15/22.1; 132/322

[56] References Cited

U.S. PATENT DOCUMENTS

| | | |
|---|---|---|
| 2,813,529 | 11/1957 | Ikse . |
| 3,056,151 | 10/1962 | Vlacancich . |
| 3,195,537 | 7/1965 | Blasi . |
| 3,235,897 | 2/1966 | Fortenberry . |
| 3,389,468 | 6/1968 | Lewis et al. . |
| 3,400,999 | 9/1968 | Goldstein . |
| 3,447,178 | 6/1969 | Pickering . |
| 3,593,707 | 7/1971 | Pifer . |
| 3,823,710 | 7/1974 | Borden ..................................... 433/216 |
| 3,987,550 | 10/1976 | Danne et al. . |
| 4,048,690 | 9/1977 | Wolfson . |
| 4,068,974 | 1/1978 | Meyer et al. . |
| 4,173,828 | 11/1979 | Lustig et al. ............................... 433/87 |
| 4,220,446 | 9/1980 | Walker .................................. 433/87 X |
| 4,236,889 | 12/1980 | Wright . |
| 4,315,741 | 2/1982 | Reichl . |
| 4,619,009 | 10/1986 | Rosenstatter . |
| 5,062,796 | 11/1991 | Rosenberg . |
| 5,098,291 | 3/1992 | Curtis et al. . |
| 5,142,723 | 9/1992 | Lustig et al. ............................. 15/22.1 |
| 5,208,933 | 5/1993 | Lustig et al. . |
| 5,321,866 | 6/1994 | Klupt ...................................... 15/22.1 |
| 5,443,321 | 8/1995 | Dolan et al. . |
| 5,476,384 | 12/1995 | Giuliani et al. . |
| 5,642,994 | 7/1997 | Chipian et al. . |
| 5,755,572 | 5/1998 | Bab et al. . |
| 5,769,553 | 6/1998 | Chaudhri et al. . |

FOREIGN PATENT DOCUMENTS

1 632 384   6/1971   Germany .

*Primary Examiner*—Nicholas D. Lucchesi
*Attorney, Agent, or Firm*—William J. Sapone, Esq.; Nims, Howes, Collison, Hansen & Lackert

[57] ABSTRACT

A fluid delivery powered toothbrush utilizes a removable/disposable neck assembly that contains a fluid reservoir, a fluid delivery system and a fluid path therein leading to a brush receptacle. No fluid is used in or passes through the toothbrush handle. Preferably a pump is located in the neck assembly and activated at the same time as the brush drive such that fluid is delivered during brushing. In one embodiment of the invention, the brush is replaced with a nozzle for providing fluid prior to or after brushing. The components for the neck assembly are disposable to minimize cross-contamination while enhancing fluid delivery to the teeth during brushing.

86 Claims, 13 Drawing Sheets

FLUID DELIVERY DENTAL CLEANING DEVICE

CROSS-REFERENCE TO RELATED APPLICATIONS

This application claims priority in U.S. Provisional Patent application No. 60/100,361 filed Sept. 15, 1998.

TECHNICAL FIELD

This invention relates to toothbrushes and more particularly to a powered toothbrush that delivers fluid such as medicament before, during, or after brushing.

BACKGROUND

In U.S. Pat. Nos. 5,276,935 and 5,373,599, commonly owned by the assignee of this invention, a medicament containing dental brush is described which releases medicament during brushing and brush fiber penetration of the gum line. The use of such a dental brush, preferably with a rotary toothbrush, provides an effective means for treating, for example, periodontal disease.

In U.S. Pat. No. 4,315,741, a toothbrush is described which has a fluid reservoir in its handle for delivering a fluid to a non-rotating working implement. In U.S. Pat. No. 5,208,933, a dental tool with liquid dispensing from a cartridge loaded into a handle is shown. U.S. Pat. No. 5,700,146 also shows a dental tool using a handle mounted cartridge. U.S. Pat. No. 5,309,590 describes a toothbrush that uses vibration for effecting fluid delivery to a brush.

Virtually all of these fluid delivery systems are of special construction, as substantial modification of the dental handle is required in each instance to accommodate a fluid reservoir and an integral fluid path. This complicates the construction and cost of such a toothbrush.

Additionally, cross-contamination is a potential problem, even where cartridges are used, because the fluid delivery path retains fluid between uses. In many instances, mixing is undesirable, and there is a concern as to sterility with fluid retained in a handle that has a mechanically useful life of many years.

SUMMARY OF THE INVENTION

It is an object of the present invention to provide a fluid delivery toothbrush that minimizes cross-contamination.

It is another object to provide a fluid delivery toothbrush that avoids fluid storage or passage through a handle.

It is yet another object to provide a fluid delivery toothbrush that delivers liquid medicament prior to, during or after brushing, using various tools to optimize effectiveness.

These and other objects of the present invention are achieved by a fluid delivery toothbrush comprising a handle having drive means therein, a mounting end having a drive coupling, a removable neck having a complimentary mounting end and a mating drive coupling for attaching to the handle, the neck having a fluid reservoir incorporated therein, fluid delivery means located in the neck in fluid communication with the reservoir, a tool mounting receptacle provided in a distal end of the neck, and, a fluid passage extending from the fluid delivery means to the tool mounting receptacle for delivering a fluid thereto.

Preferably, a brush is mounted in the tool receptacle, the brush being rotatable such that centrifugal force acts as the fluid delivery means for drawing the fluid to the brush tips for distribution on the brush contacted surfaces. Alternatively, pump means can be provided to deliver fluid to the brush.

The present invention thus provides for impregnation of the brush during operation by means of the fluid reservoir in the neck.

The reservoir may be refillable, and the brushes replaceable, such that various fluids may be applied using the invention. Different fluids can be used in different neck assembles, interchangeably mounted on a common handle. However, sealed reservoirs may be used, for example, with medicaments for unit dosing with disposal of the neck thereafter.

The threat of cross-contamination is minimized, as the neck can be disposed of after a single use, or after multiple uses by an individual. In addition, no fluid is contained in or passed through the handle, and contamination of the handle is avoided.

In one embodiment of the invention, the fluid delivery means comprise pump means having at least one resilient wall responsive to hand pressure such that the user can impregnate the brush and apply the medicament at selected times prior to, during or after brushing.

In another embodiment of the invention, a pump, driven mechanically, electrically or otherwise, is connected to the reservoir, for supplying fluid to the brush mounting receptacle prior to, during or after brushing.

In another embodiment of the invention, the brush can be exchanged for either an irrigator nozzle or tongue scraper which mount in the tool receptacle to provide irrigation without a brushing action or during tongue scraping.

Preferably, the neck is separated into two components, a pump/reservoir portion and a drive neck portion, so that a pump/reservoir portion can be removed for direct connection by the drive neck to the handle. This allows for operation in a non-fluid delivery mode, or for interchange with another pump/reservoir portion for supplying a different fluid.

In all cases, the neck contains all the elements necessary for fluid delivery, the housing incorporating mechanical and electrical components for powering the toothbrush. The neck components are of low cost construction and are thus disposable. One uses a common housing with either fluid delivery necks or non-fluid delivery necks so that the most expensive portion of the powered toothbrush avoids contamination by or in association with fluid delivery or brushing.

DETAILED DESCRIPTION OF THE INVENTION

Figure 1A:
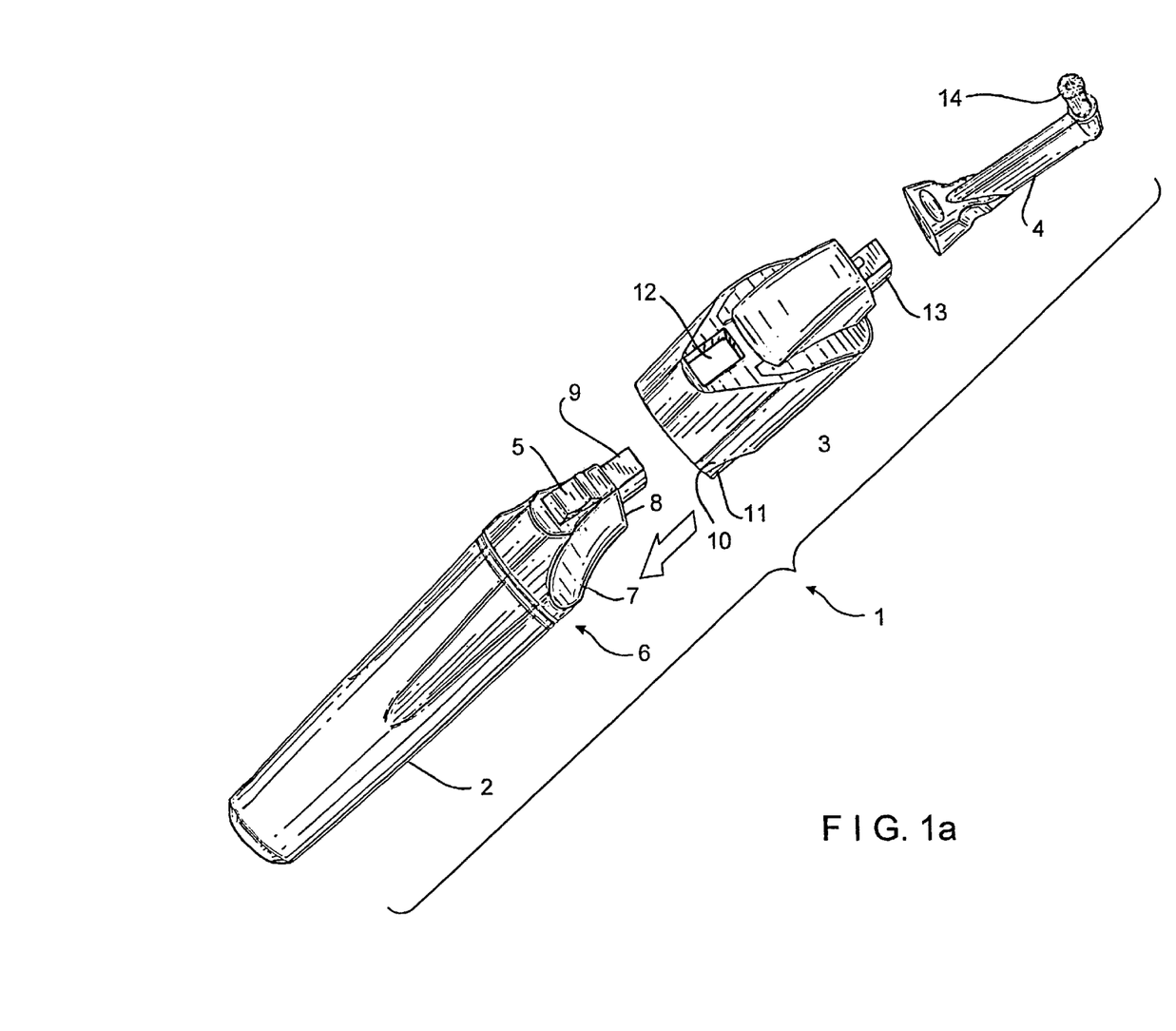
FIG. 1a is a perspective exploded view of a fluid delivery toothbrush in accordance with the present invention.

Referring to FIG. 1a, a powered toothbrush 1 has a handle 2, a removable pump/reservoir section 3 and a drive neck section 4. By "powered toothbrush" is meant any apparatus for use by an individual for cleaning teeth that uses electrical power to enhance cleaning by imparting rotation, oscillation, vibration, etc. to supplement normal manual brushing motions. Such powered toothbrushes are well known, and are relatively expensive as compared to manual toothbrushes, because of their mechanical/electrical components.

The handle 2 has a conventional motor (not shown) disposed therein, activated by a switch 5. A forward portion 6 of the handle has sloped side surfaces 7, a face surface 8 and a coupling 9 for attachment of the pump/reservoir section 3 thereto.

Figure 1B:
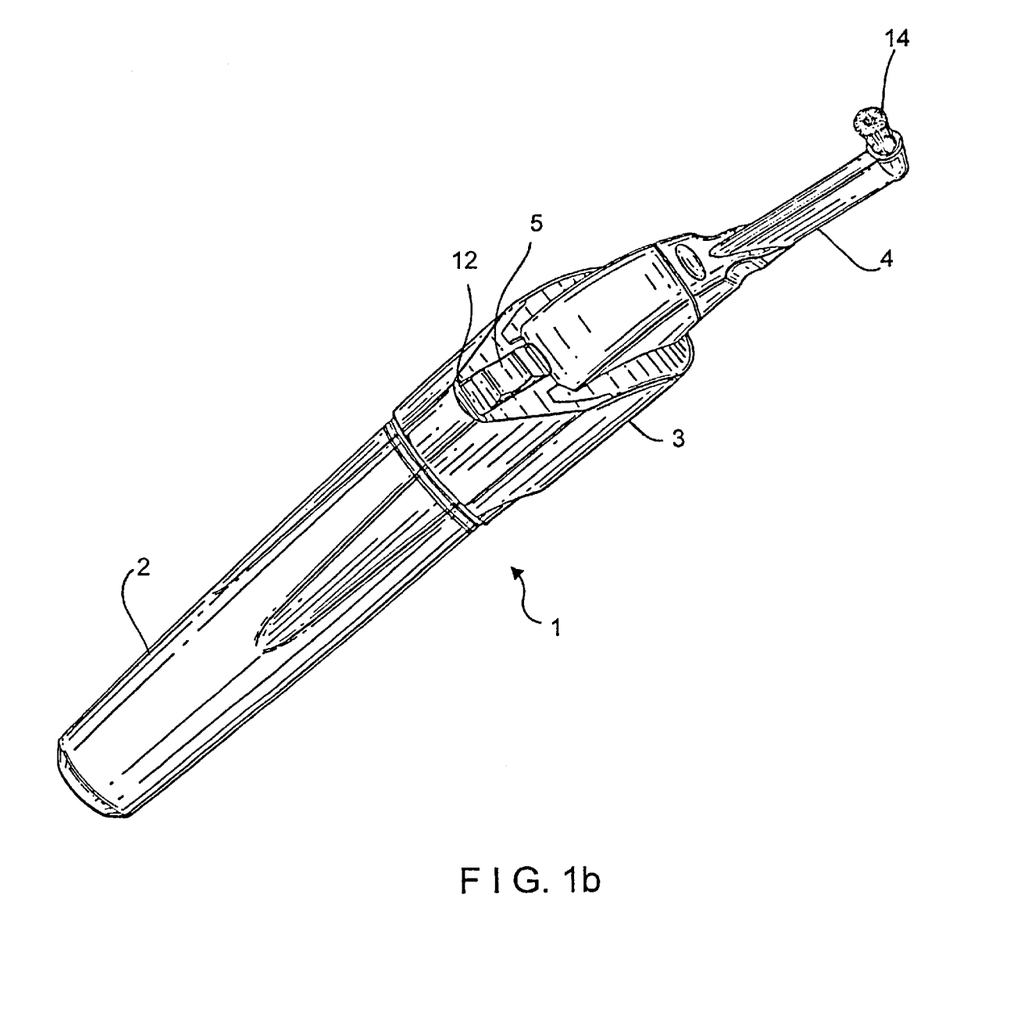
FIG. 1b shows the toothbrush as assembled.

The removable pump/reservoir section 3 has complementary sloped surfaces 10 in an inner chamber 11 for receiving the sloped side surfaces 7 of the handle when the pump/reservoir 3 is fitted on the forward portion 6 of the handle. An access port 12 receives the switch 5 therein, as best seen in FIG. 1b.

The pump/reservoir section 3 has a coupling 13 which receives the drive neck section 4 thereon. The drive neck section has a brush 14 that may be removable. FIG. 1b shows the assembled toothbrush.

Figure 2:
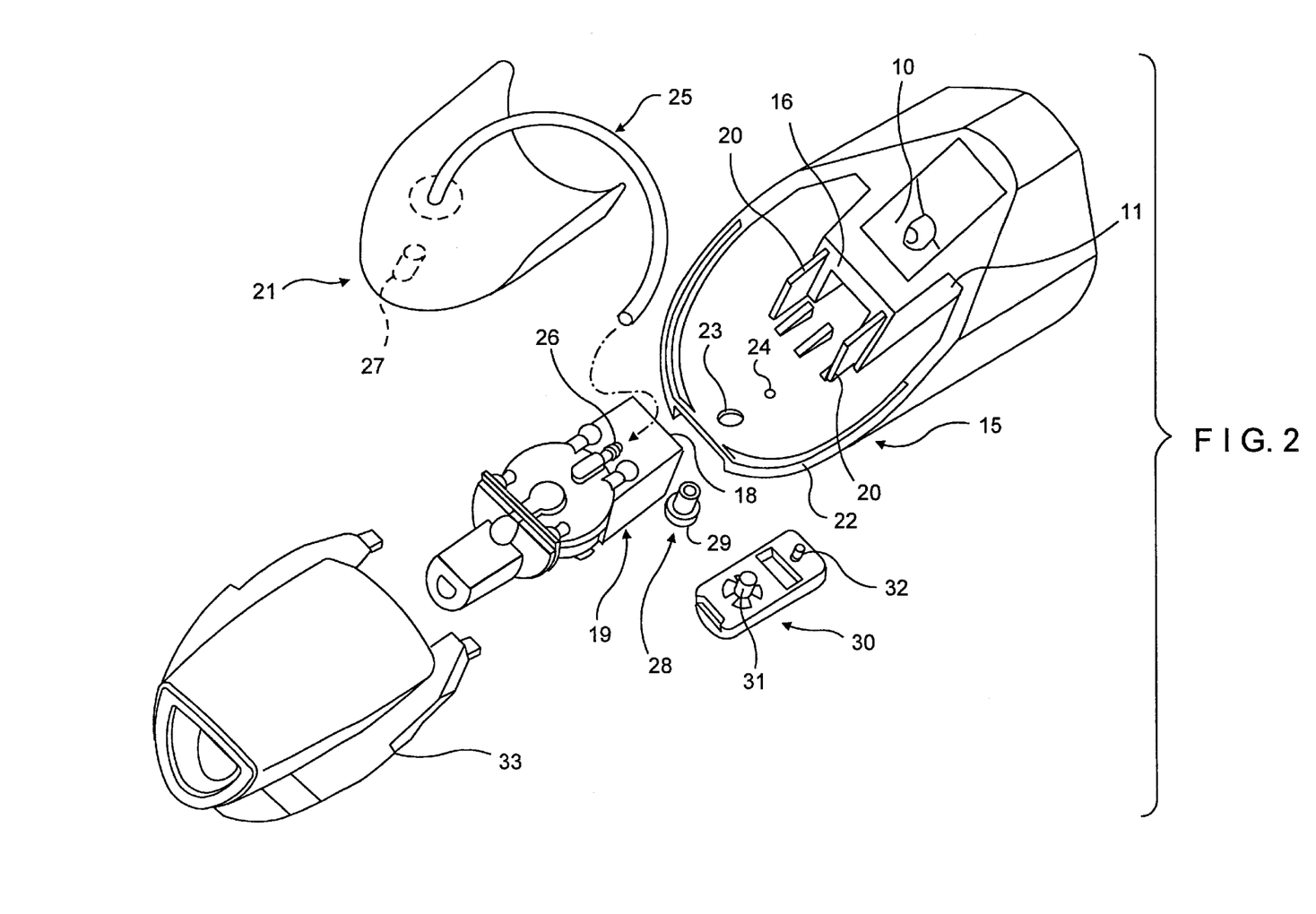
FIG. 2 is a exploded view of the pump/reservoir section.

Referring to FIG. 2, an exploded view of the pump/reservoir section 3 is shown. The section has a housing 15 with the complementary sloped surfaces 10 in the inner chamber 11. In addition, the housing has a wall 16 with an opening 17 for receiving the coupling 9 extending from the handle. This coupling enters a mating socket 18 in a pump assembly 19, which is mounted adjacent the wall 16, between a pair of sidewalls 20. A pliable bladder 21 fits beneath the pump assembly, resting on a curved wall 22, that has a pair of holes 23 and 24 therein. The bladder has a tube 25 that connects to an entry port 26 on the pump assembly. The bladder further has an opening 27 which receives an eyelet 28 having a collar 29, the eyelet passing through the hole 23. A resilient flip lid 30 has a plug 31 received in the eyelet for preventing fluid from leaking out of the bladder. The flip lid is attached to the housing 15 by a locating peg 32 that is received in the hole 24. A cover 33 fits over and covers the pump assembly and reservoir, to complete the assembly.

The bladder is preferably pliable to allow collapse as fluid is discharged. Of course, a rigid wall bladder could also be used with a vent to let air enter as the fluid is discharged. With this embodiment of the invention, the pliable bladder is preferred to avoid liquid hold-up or leakage through the vent.

Figure 3A:
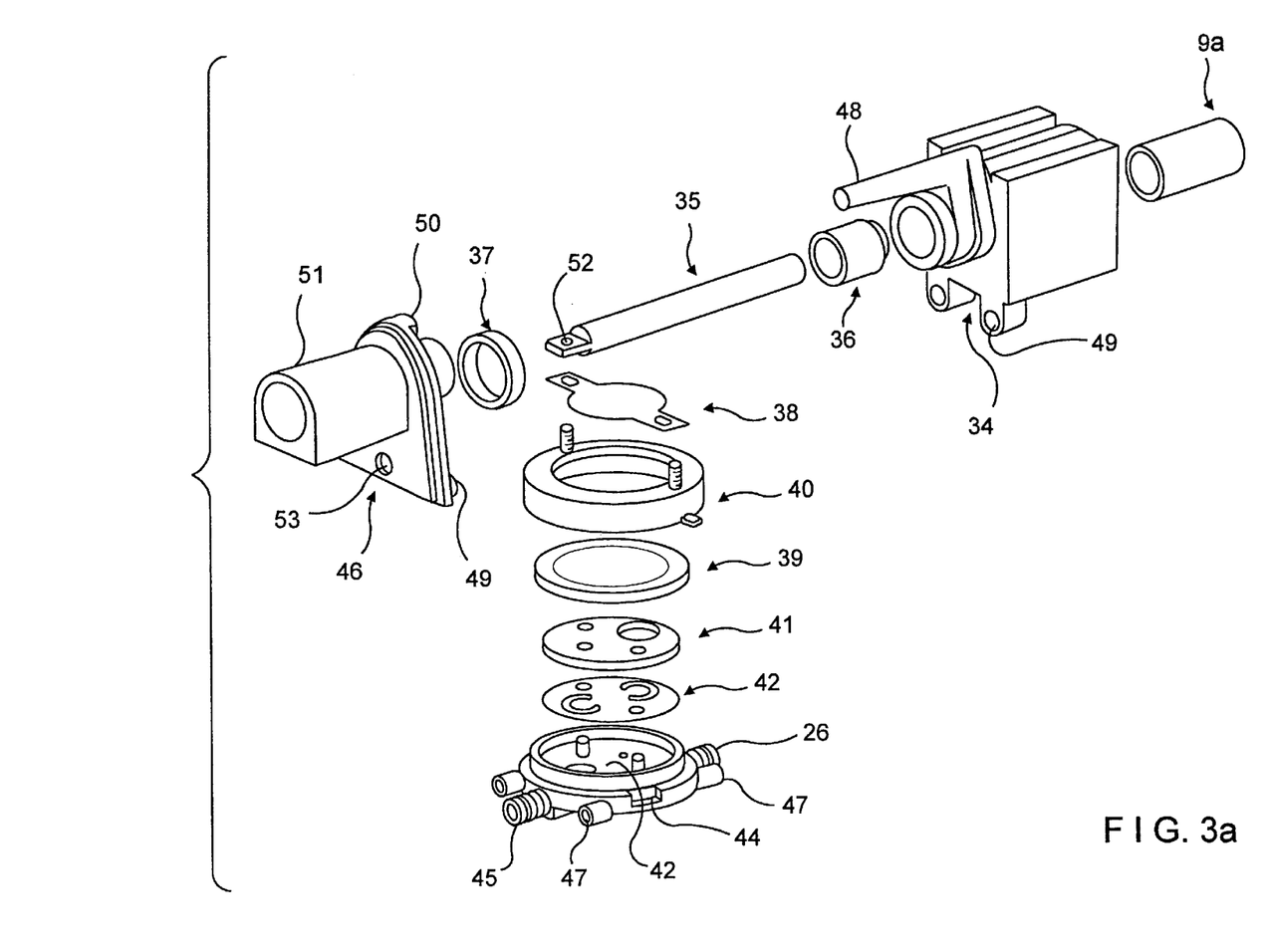
FIG. 3a is a exploded view of the pump assembly.

Referring to FIG. 3a, the pump assembly 19 is shown in exploded form. The pump assembly has a chassis 34 through which a shaft 35 is connected to the coupling 9a. The shaft is rotatably supported by a bearing 36. A cam 37 is mounted on the shaft, the cam being in contact with a cam follower 38 that rests on a flexible diaphragm 39, so that as the cam rotates, the diaphragm is alternately compressed and released. The cam follower is placed on a diaphragm cover 40, that holds the diaphragm in place. A backing plate 41 provides a fluid passage, acting with a reed valve 42 in response to the diaphragm, such that each pulse of the diaphragm first draws fluid through the entry port 26 into a pump chamber 43 in a pump body 44, and then discharges the fluid through a exit port 45. Thus, when the switch on the handle is activated, the shaft turns the cam, causing fluid to be pumped.

A front chassis 46 completes the assembly, locating pegs 47 in the pump body and a support rod 48 being received in complementary sockets 49 and 50 to hold the assembly together. The front chassis 46 has a mounting coupling 51 within which a forward end 52 of the shaft 35 is located. A passage 53 receives the pump exit port therein.

Figure 3B:
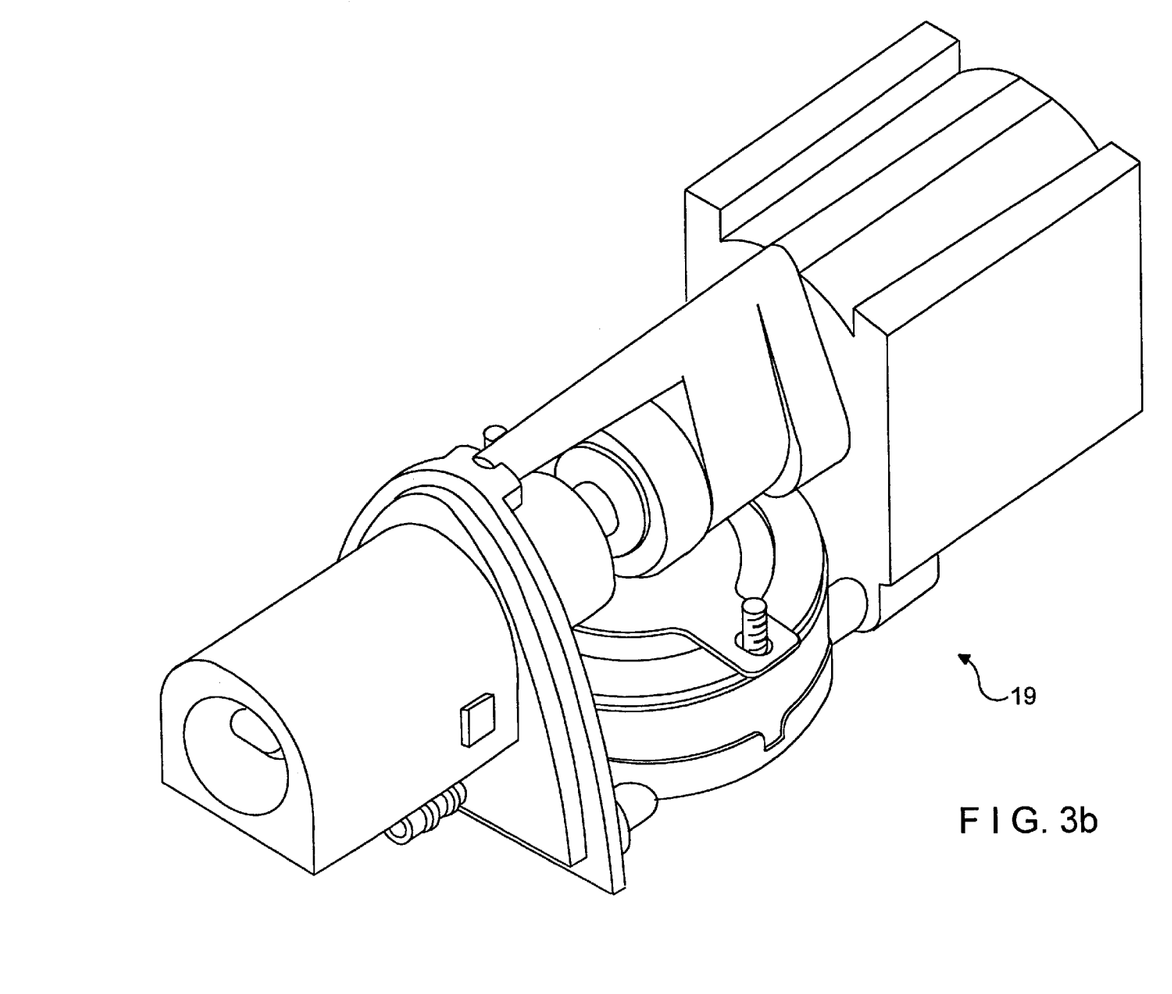
FIG. 3b is a view of the completed pump assembly.

FIG. 3b shows the completed pump assembly 19.

Figure 4A:
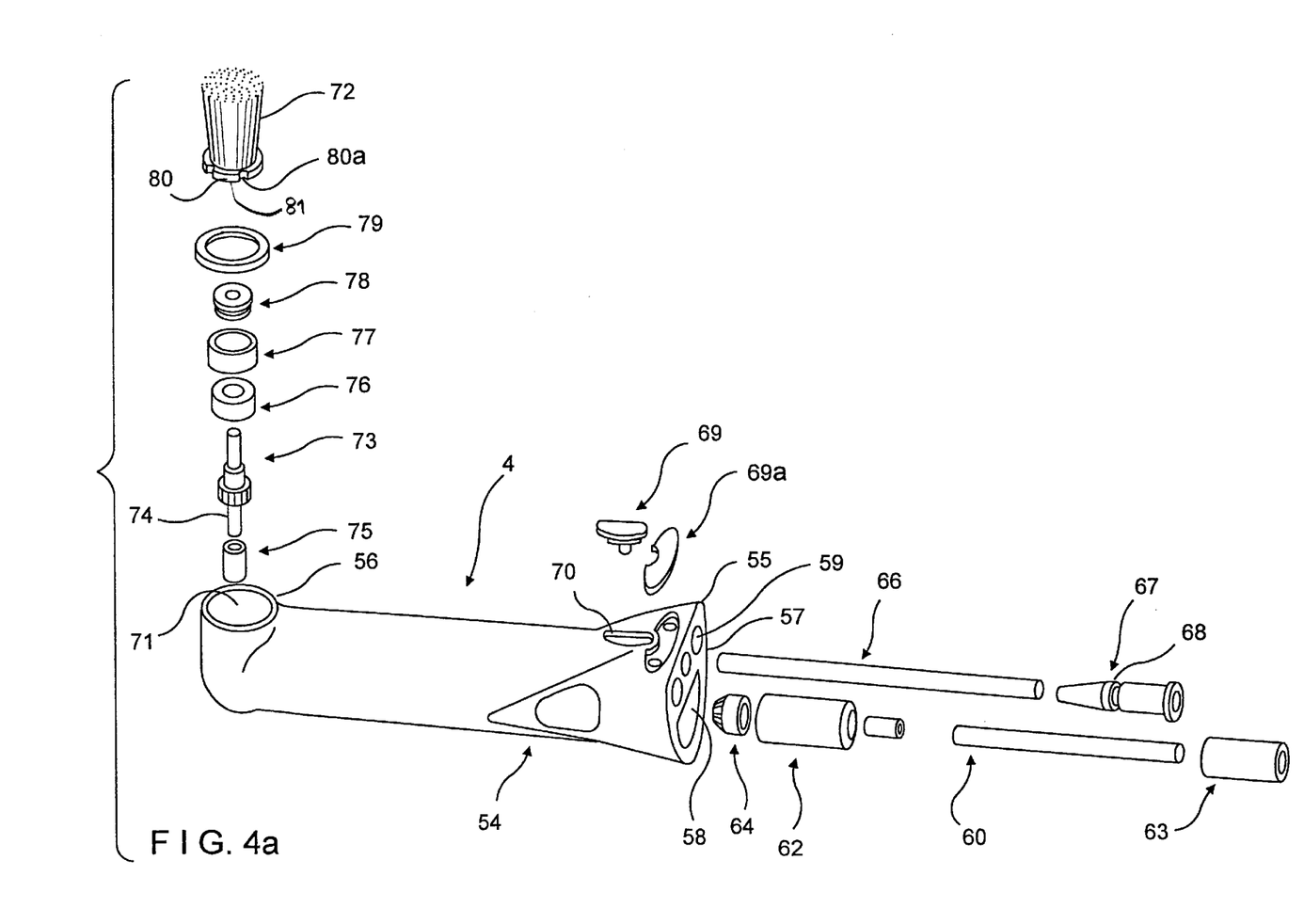
FIG. 4a is a exploded view of the drive neck.

Referring to FIG. 4a, the drive neck 4 is shown in an exploded view. The drive neck has a housing 54 having a drive mounting end 55 and a tool receiving end 56. The drive mounting end has a mounting face 57 with a drive shaft entrance 58 and a tube entrance 59, a drive shaft 60 placed in a drive tunnel 61. The shaft is rotatably supported by a bearing 62, and has a coupling 63 for connecting to the shaft end 52 extending from the pump reservoir section. A gear 64 is mounted at a proximal end of the drive shaft. Running parallel to the drive shaft tunnel 61 is a fluid delivery tunnel 65 within which a tube 66 resides. The tube 66 is mated to a duckbill seal 67 having a groove 68 engaged by a retainer 69 that passes through an opening 70 in the housing 54.

The tool receiving end 56 includes a passage 71 at a right angle to the drive shaft tunnel. Within this passage are located the components for rotating a tool which in this instance is a brush 72. A shaft 73 has an end 74 received in a bearing 75 held in the passage 71. A gear 76 is mounted on the shaft, to engage the gear 64 on the drive shaft. A retaining washer 77 receives a shaft seal 78 for holding the tool drive assembly in the passage. An optional distribution ring 79, which may be made of a resilient material such as rubber, surrounds a base 80 of the brush 72 to distribute fluid around the periphery of the brush. The brush in this embodiment has grooves 80a in the periphery of the base to assist in fluid distribution. The brush has a receptacle 81 for receiving an end 82 of the shaft 73 therein. The ring is optional as fluid distribution can be achieved alternatively by establishing somewhat close tolerances between the brush base and the passage sidewalls.

Figure 4B:
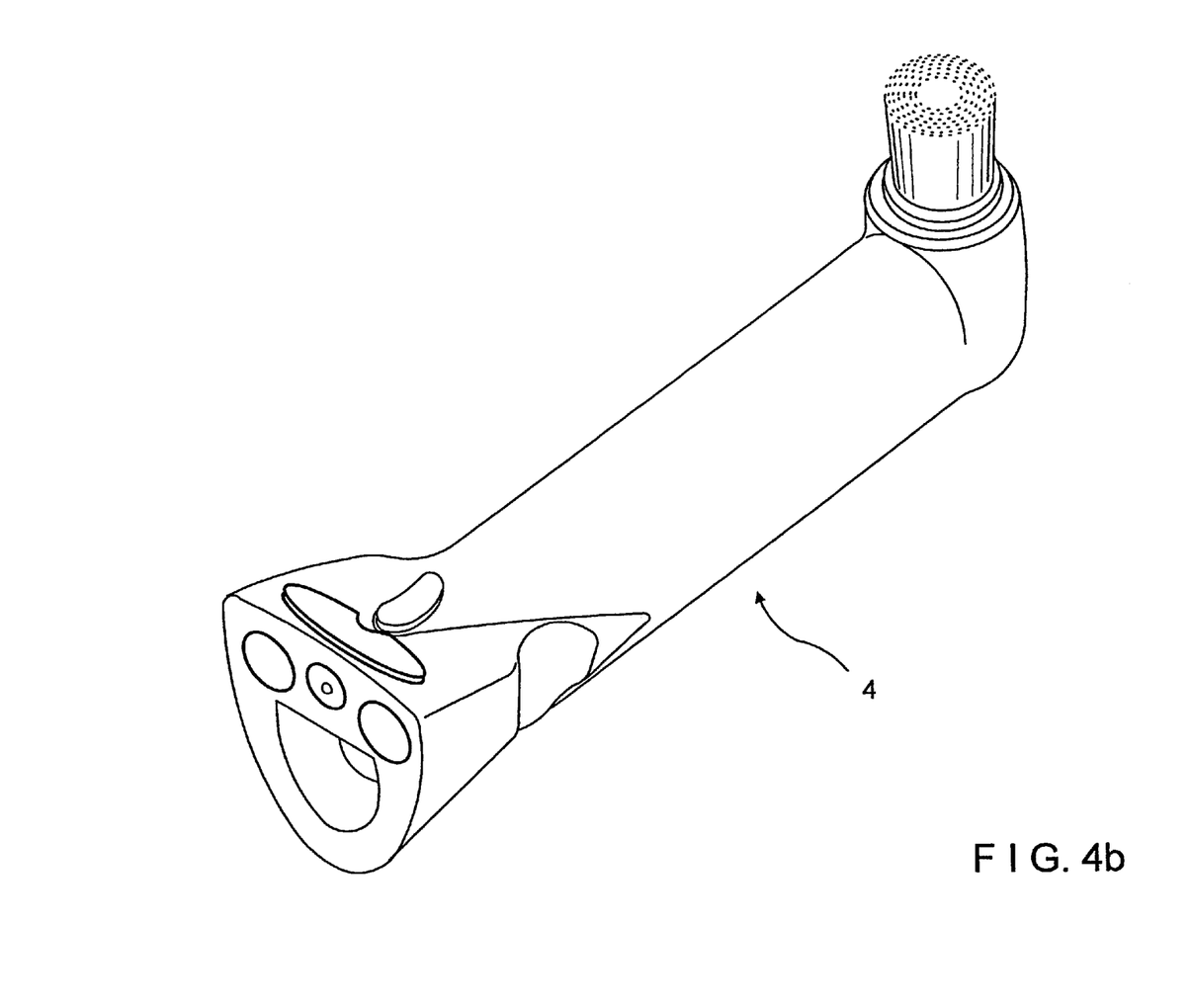
FIG. 4b shows the drive neck as assembled.

Referring to FIG. 4b, the completed drive neck assembly 4 is shown.

Figure 5A:
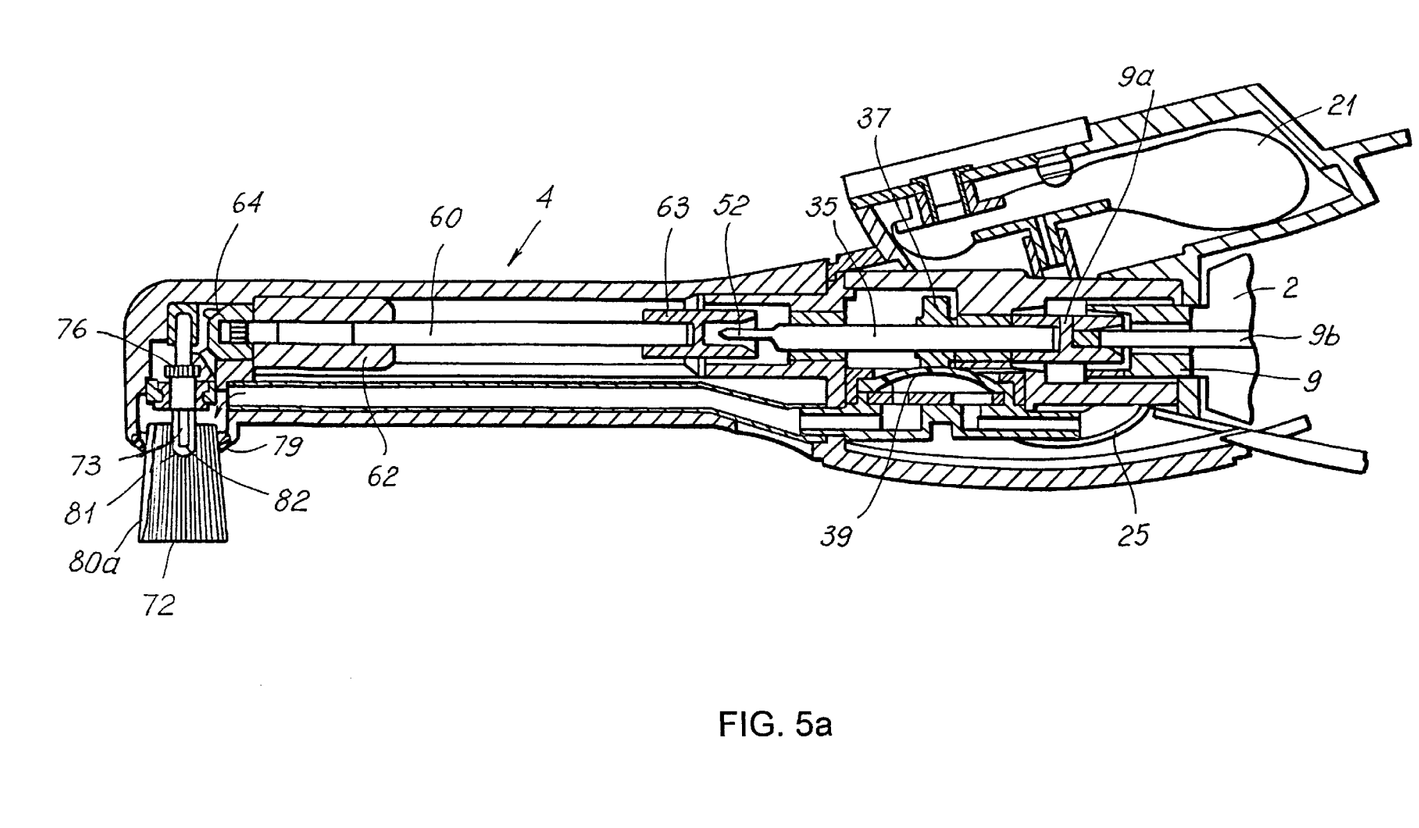
FIG. 5a shows the fluid delivery toothbrush in cross section.

Referring to FIG. 5a, the assembled components are shown in cross section. A drive shaft 9b, which passes through the coupling 9 in the housing 2, engages the coupling 9a, which in turn, causes rotation of the shaft 35. The end 52 of the shaft 35 is engaged to the coupling 63 in the neck assembly 4, driving the shaft 60. The shaft 60, supported for rotation by the bearing 62, turns the gear 64, which is engaged with the gear 76, driving the shaft 73 and the brush 72.

As the drive shaft 35 rotates, the cam 37 acts on the diaphragm 39 to cause pumping of a fluid from the bladder 21 to the brush 72.

Figure 5B:
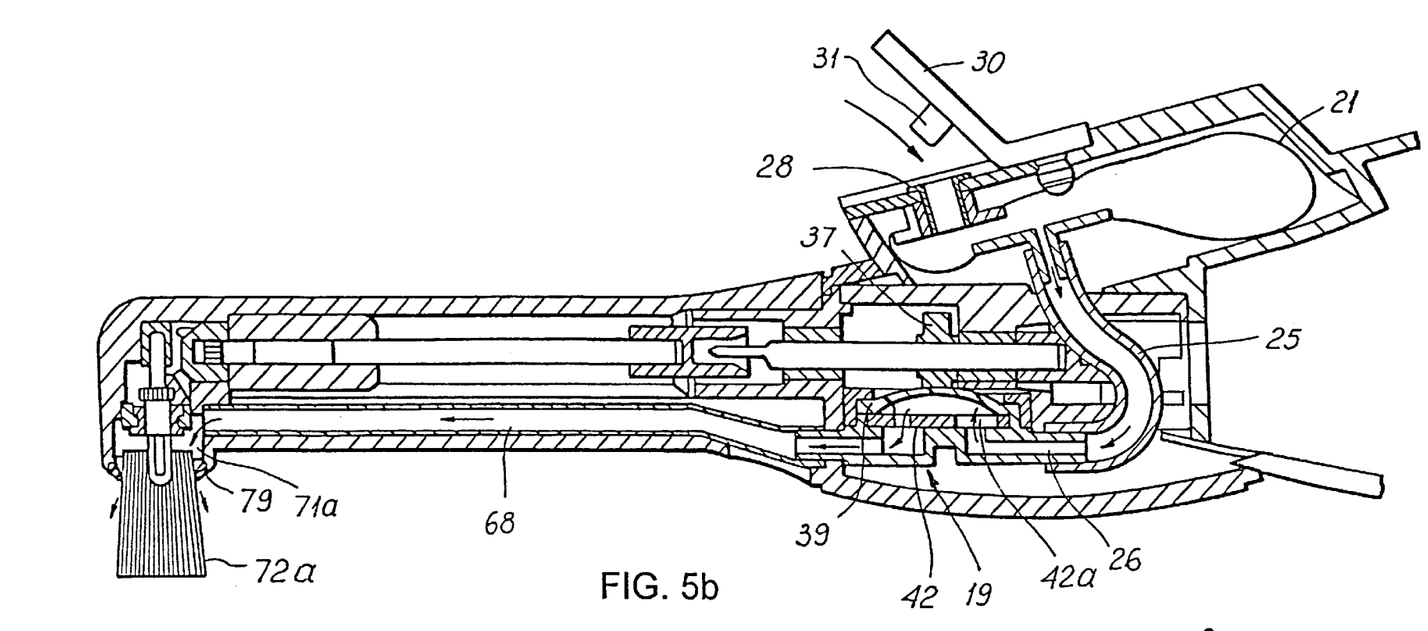
FIG. 5b shows the fluid delivery toothbrush in cross section illustrating the fluid path.

Referring to FIG. 5b, the fluid delivery path is illustrated. The flip lid 30 is raised to remove the plug 31 from the eyelet 28. This allows fluid to be added to the bladder. The tube 25 supplies the fluid to the entry port 26 for the pump assembly 19. As the cam 37 acts on the diaphragm, the reed valve 42 has elements 42a and 42b which allow fluid to flow in one direction, from entry port 26 to the exit port 45. The fluid then flows to the tube 68.

The tube 68 terminates in the passage 71, forming a chamber 71a beneath and adjacent the base 80 of the brush 72, below the distribution ring 79, which acts as a seal for the chamber. Fluid passes by the distribution ring, along the grooves 80a in the brush base for delivery to the brush tip.

The drive neck may mount either to the handle directly or to the pump reservoir section, so that brushing with or without fluid delivery are possible. Also the neck can be replaced separately from the pump reservoir section, for example, so different persons can use a common handle without cross-contamination.

Figure 6A:
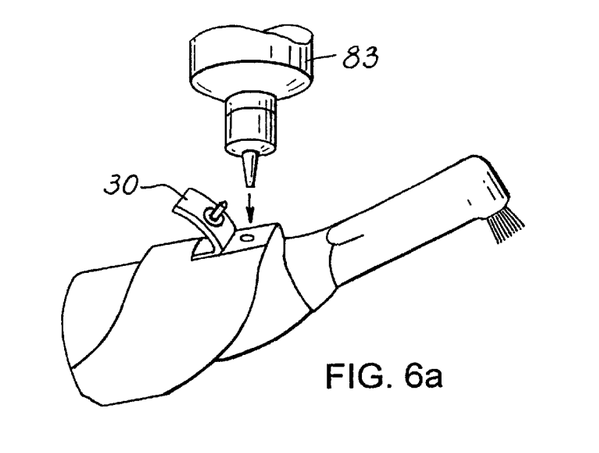
FIG. 6a shows the reservoir receiving a fluid.

Referring to FIG. 6a, the flip lid 30 is shown in the open position, a fill bottle 83 used to fill the bladder 21 in the pump reservoir section. In this way, various fluids such as medicaments, mouthwash, liquid dentifrice, etc. can be provided during brushing.

Figure 6B:
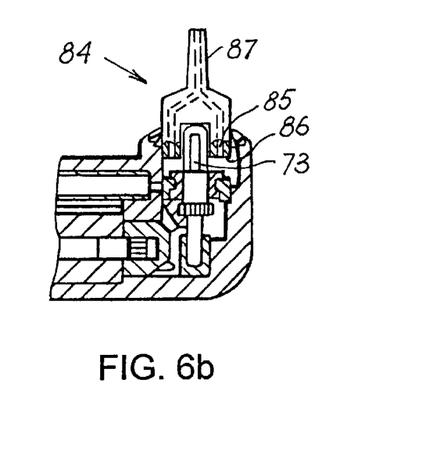
FIG. 6b shows a irrigator nozzle; and, FIGS. 6c and 6d show a tongue scraper attachment.

Referring to FIG. 6b, the brush can be removed and replaced by a different tool such as a nozzle 84, which fits in its place to provide direct irrigation prior to or after brushing. The nozzle 84 slides onto the shaft 73, and has openings 85 in a base 86 for delivery of fluid to a tip 87 of the nozzle.

Figure 6C:
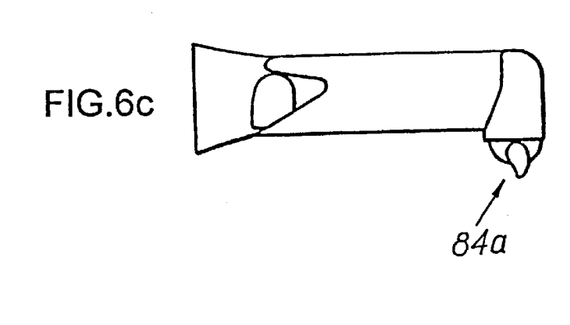
Figure 6D:
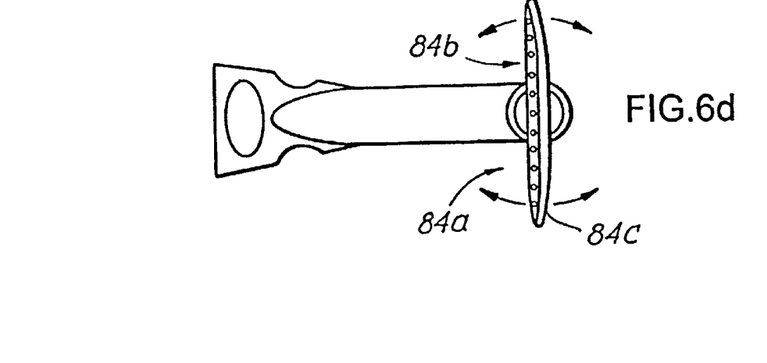

Referring to FIGS. 6c and 6d, the brush can be removed and another tool such as a tongue scraper 84a fitted in its place. The tongue scraper has outlets 84b in an edge 84c which provide direct irrigation as the scraper traverses the tongue or other mouth surfaces. The tongue scraper can be static or have a drive coupling for adding mechanical action to enhance the scraping effect.

Advantages of the invention are that the reservoir is an integral part of the removable/disposable neck so that there is no possibility of cross-contamination. There are few moving parts to wear out or malfunction, and the parts used are of relatively low cost to produce and assemble. The bladder could be composed of any resilient material, such as natural or synthetic rubber, silicone elastomer or a fluoroelastomer, or if rigid, be made of any rigid plastic. The bladder could also be sized to contain only a "unit dose", so that it is emptied after each use, to reduce the chance of the fluid getting stale, contaminated, or mixed with another fluid. Flushing with water or an antimicrobial is also readily accomplished by filling and powering the toothbrush. When antimicrobial fluids are used, the fluid passages would be substantially protected from contamination.

In one variation, the reservoir is provided with no fill opening, so that a dedicated dosage of a particular fluid is prepackaged during assembly, under conditions promoting sterility. Once delivered, the pump/reservoir section is disposed of. This reduces the possibility of contamination.

It should be understood that the reservoir could also be of a size to accept multiple doses. If a pump is used, it could also be activated by a different drive system, whether for powering a rotary, oscillatory, vibratory, or mechanical tooth cleaning action, as different components could easily be chosen to effect a pumping action.

Figure 7:
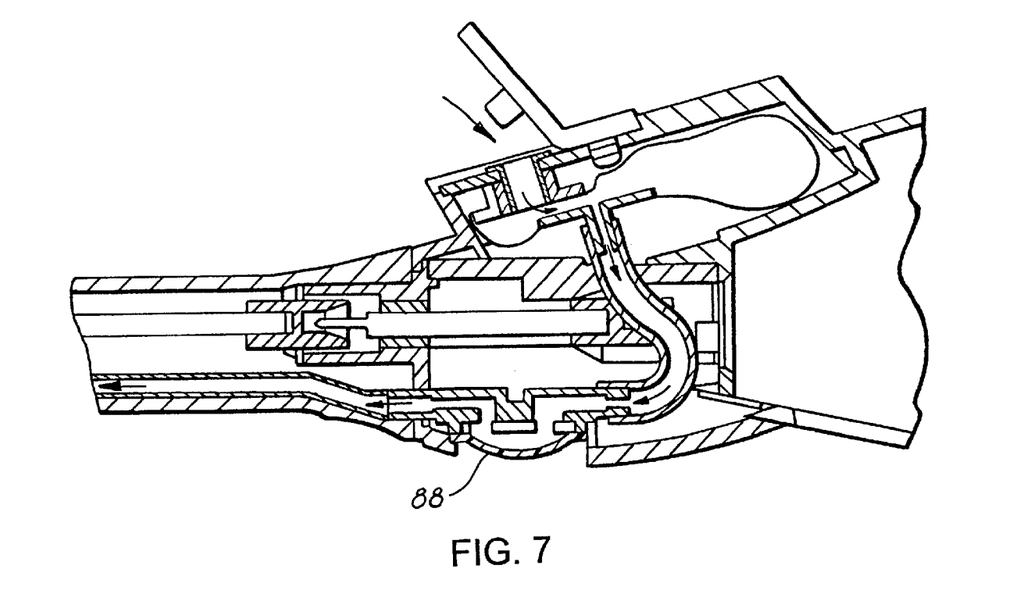
FIG. 7 is an alternative embodiment of the invention.
Figure 8:
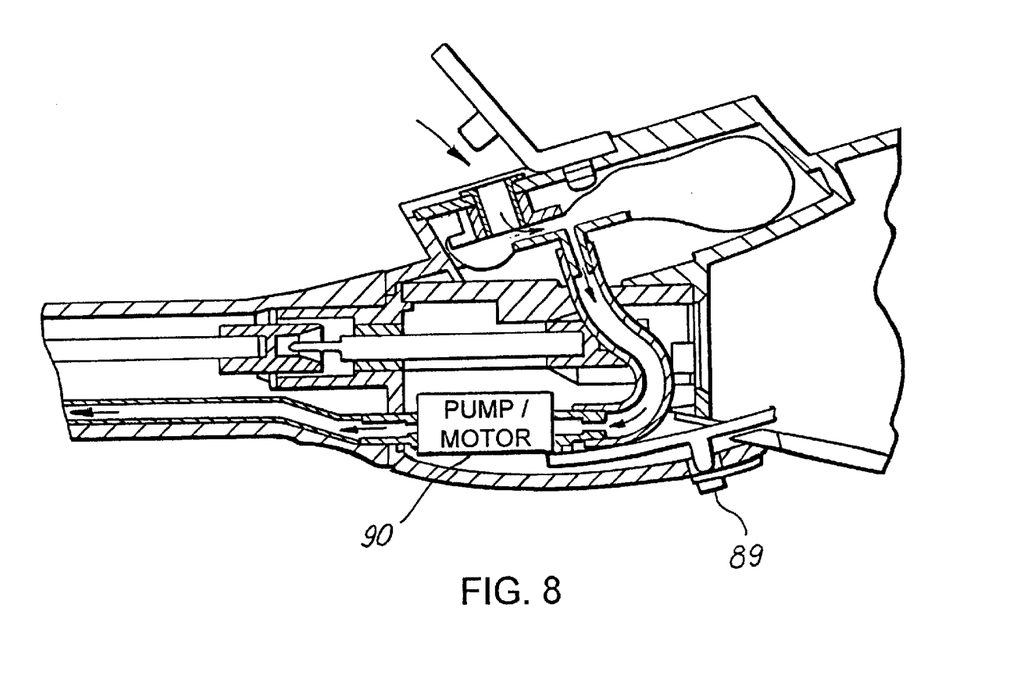
FIG. 8 is another alternative embodiment of the invention.

Manual pressure on the pump diaphragm is also an available delivery means, as illustrated in FIG. 7 where a pump diaphragm 88, rather than being driven by the cam, is exposed for activation by finger pressure. In another alternative, shown in FIG. 8, a separate switch 89 is connected to a pump/motor 90 for optionally powering the pump separately from the brushing motor so that fluid can be selectively delivered prior to, during or after brush motor activation.

As described above, the brush can be interchanged with an irrigating nozzle which provides for fluid delivery alone, without brushing action. Further, a neck portion with the fluid delivery path could selectively be used directly on the handle such that one can apply fluid, for example once per day or on alternate days, while switching to a non-fluid delivery neck portion at other times. This conserves the fluid or allows for the exchange of reservoirs with different fluids without cross-contamination.

Figure 9A:
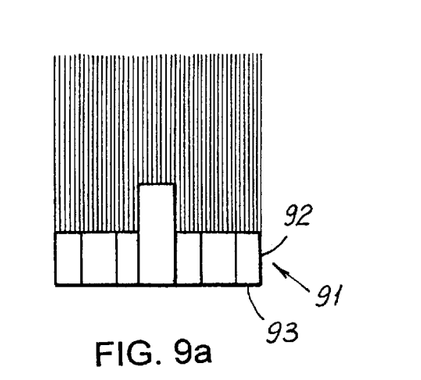
FIGS. 9a and 9b show a brush with through passages.
Figure 9B:
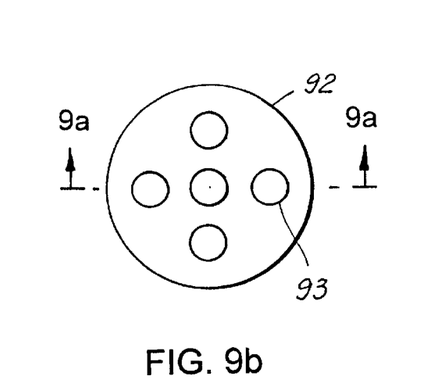
Figure 9C:
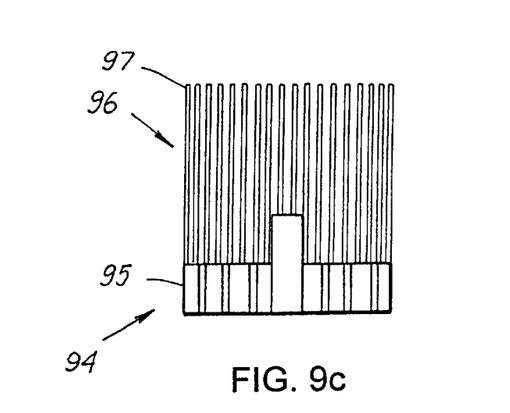
FIGS. 9c and 9d showing a brush made of hollow fibers.
Figure 9D:
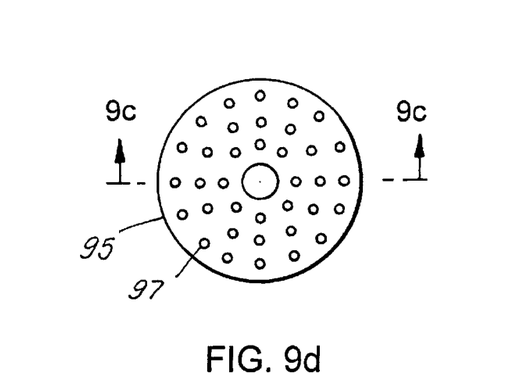

While a conventional brush can be used with the invention, FIGS. 9a–9d show alternative brushes for optimizing fluid delivery. FIGS. 9a and 9b show a brush 91 having a base 92 incorporating passages 93 for providing fluid within the brush tuft. FIGS. 9c and 9d show a brush 94 having a base 95 with a brush tuft 96 made from or including a plurality of hollow fibers 97 that extend through the base for delivering fluid to the fiber tips. In each case, the fluid enters the chamber behind the brush, and from the chamber, the fluid passes either around, in-between, or through the brush fibers, until it reaches the ends of the brush where it would contact the teeth and gums. The distribution ring, if present, seals against the rotating brush and would perform as a wiper or guide to channel the fluid into the brush, also preventing fluid such as saliva from leaking into the chamber.

Figure 10:
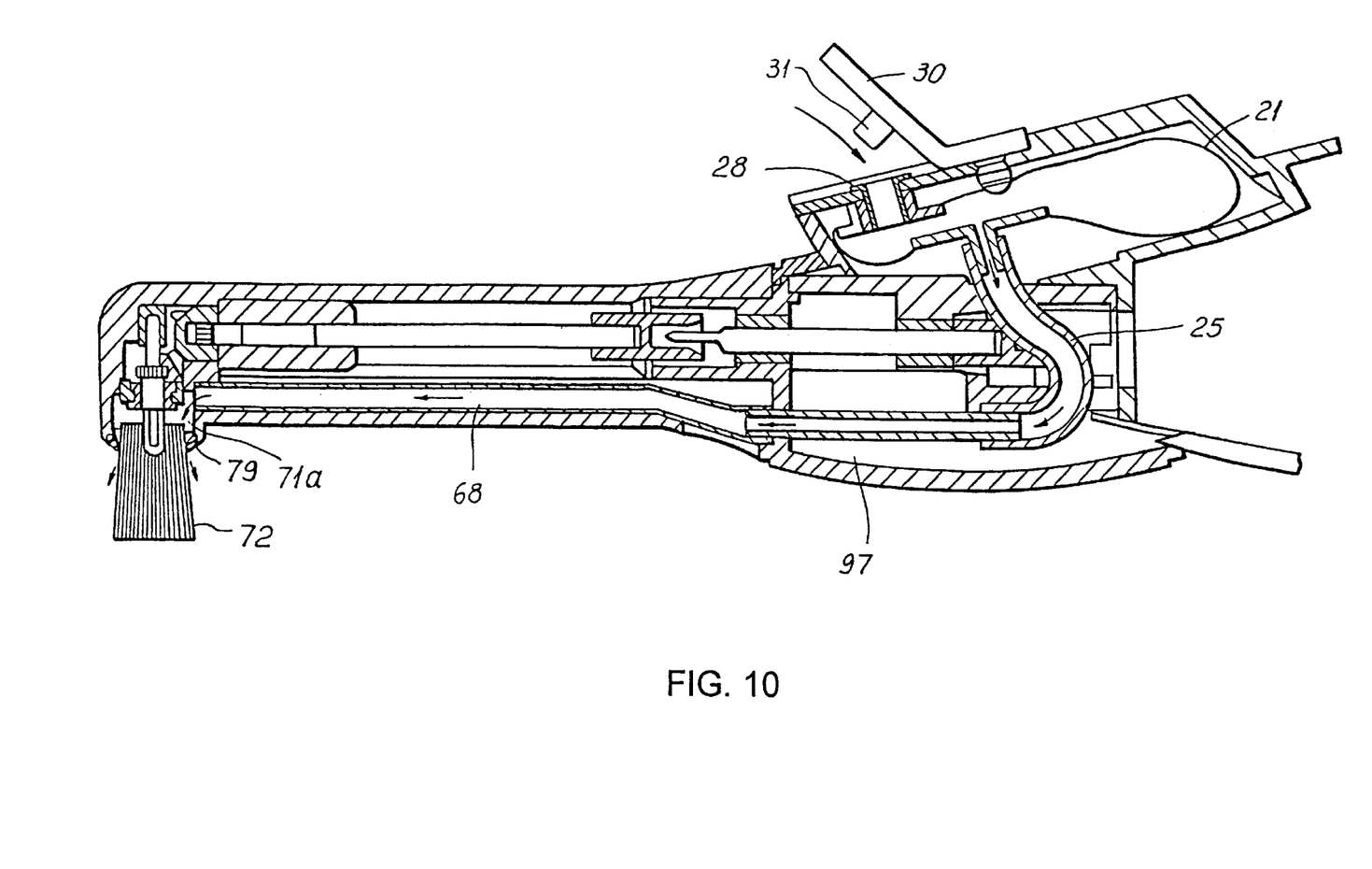
FIG. 10 is another embodiment of the invention which utilizes capillary action to effect fluid delivery.

Referring to FIG. 10, another embodiment of the present invention is shown. Here, the pump assembly 19 is avoided, and instead, there is a through coupling 97 for connecting the bladder 21 to the passage 71 and specifically to the chamber 71a beneath the brush. Fluid delivery is accomplished by the fluid entering the chamber by gravity when the toothbrush is held horizontally, such that the fluid contacts a lower portion 98 of the brush fibers. Because of capillary action, the fluid wetting the fibers is drawn out of the chamber, automatically providing fluid delivery during brushing. Where a rotating brush is used, centrifugal force increases the delivery rate by promoting throw-off of the fluid from the rotating fibers.

Figure 11A:
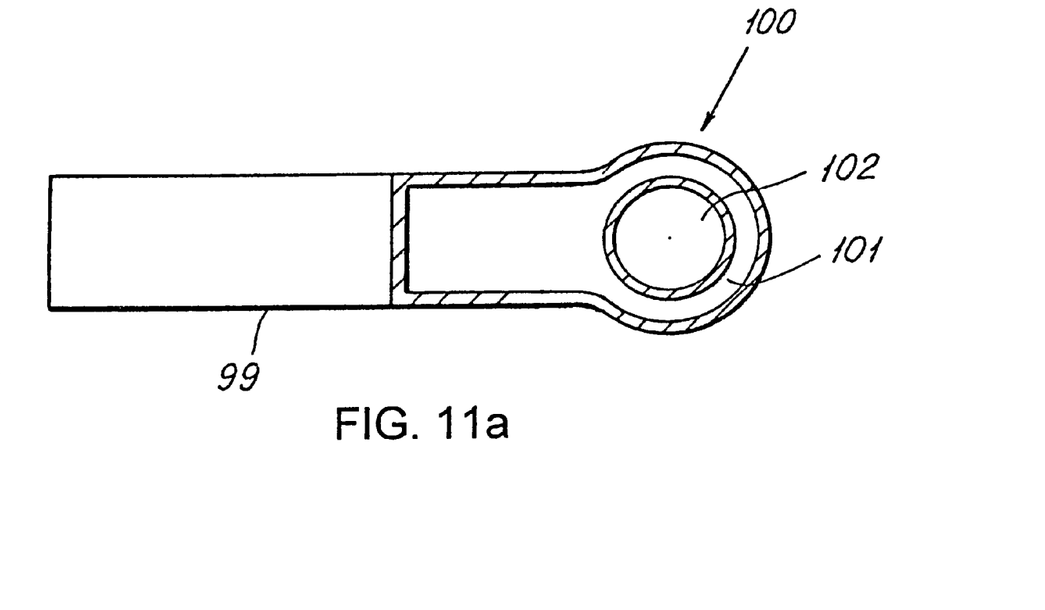
FIGS. 11a and 11b show another embodiment of the invention utilizing a concentric fluid reservoir.
Figure 11B:
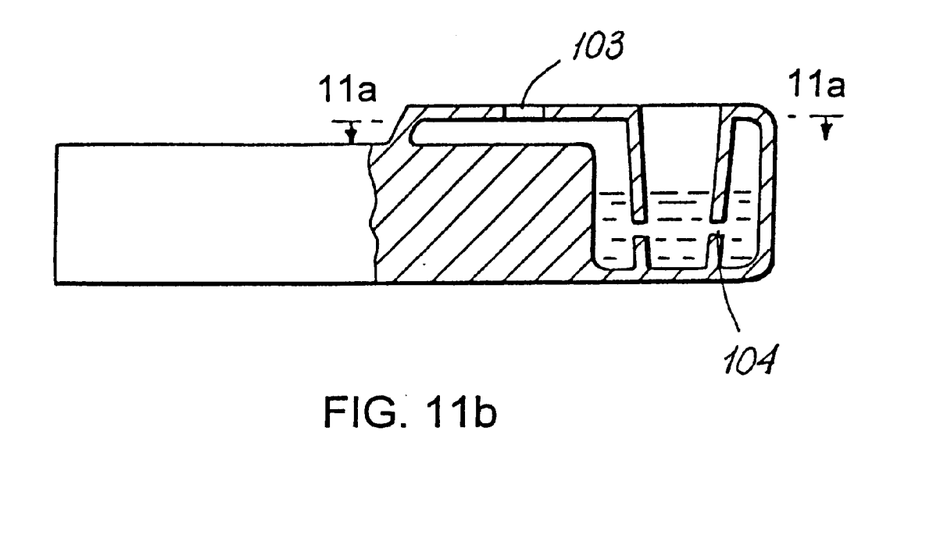

Referring to FIGS. 11a and 11b, another version of a gravity feed system for fluid delivery is shown. A neck 99 has a head portion 100 that is enlarged so as to provide a concentric reservoir 101 that surrounds a chamber 102. For ease in illustration, the tool and drive components have not been shown but these would be understood to be includable in the neck 99. A fill port 103 leads to the reservoir 101 which surrounds the chamber 102. Openings 104 provide the fluid delivery means for fluid communication between the reservoir and the chamber. Thus, regardless of orientation, fluid will always be accessible to a brush located in the chamber, where capillary action could assist in drawing fluid out of the chamber for delivery during brushing.

Fluids usable with the present invention include those listed in the applicant's prior patents as well as any liquid mouthwash, dentifrice, medicament, etc.

While various embodiments have been shown and described, it will be understood by those skilled in the art that the invention is not limited to these particular embodiments and that changes can be made without varying from the scope of the present invention and in particular, various features and structures can be interchanged among the illustrated embodiments.

We claim:

1. A fluid delivery dental cleaning device comprising a handle having drive means therein and a mounting end having a drive coupling, a removable neck having a complementary mounting end and a mating drive coupling for attaching to the drive coupling on the handle, a tool mounting receptacle located at an end of the neck, a fluid reservoir composed of a resilient material incorporated in the neck, fluid delivery means in fluid communication with the reservoir and with the tool mounting receptacle for supplying a fluid thereto.

2. The dental cleaning device of claim 1 wherein the neck is separable into two sections, a reservoir section and a separable drive neck section, the reservoir section housing the fluid reservoir and fluid delivery means, a reservoir drive coupling provided on a forward end thereof, the drive neck having the tool mounting receptacle and a complimentary drive coupling for attaching to the reservoir section.

3. The dental cleaning device of claim 1 wherein the fluid delivery means is a diaphragm pump.

4. The dental cleaning device of claim 3 wherein a diaphragm portion of the diaphragm pump is accessed through an opening in the neck for activation by finger pressure.

5. The dental cleaning device of claim 1 wherein the fluid reservoir has a entry port for placing fluid therein.

6. The dental cleaning device of claim 1 further comprising a cam mounted on a drive shaft extending from the drive coupling through the neck, the cam in contact with the fluid delivery means for effecting a pumping action during rotation of the drive shaft.

7. The dental cleaning device of claim 1 wherein the tool mounting receptacle has a fluid receiving chamber adjacent a base of a tool mounted therein.

8. The dental cleaning device of claim 1 further comprising a distribution ring located around the tool mounting receptacle.

9. The dental cleaning device of claim 1 wherein the fluid delivery means is a pump/motor, a switch for activating the pump/motor located on the removable neck.

10. The dental cleaning device of claim 1 wherein the fluid reservoir is concentric to the tool mounting recepticle.

11. The dental cleaning device of claim 1 further comprising a distribution ring located around the tool mounting receptacle.

12. The dental cleaning device of claim 1 further comprising a tool selected from the group consisting of a brush, a tongue scraper and a nozzle.

13. The dental cleaning device of claim 1 wherein a brush is mounted in the tool mounting receptacle.

14. The dental cleaning device of claim 13 wherein the brush has a base having grooves about an outside periphery thereof for passing fluid thereby.

15. The dental cleaning device of claim 13 wherein the brush has a base having holes therethrough.

16. The dental cleaning device of claim 13 wherein the brush has a tuft containing tubular fibers having open ends extending through a base of the brush for passing a fluid therethrough.

17. The dental cleaning device of claim 1 further comprising a tongue scraper mounted in the tool mounting receptacle, the tongue scraper having a edge, openings provided in the edge for delivering fluid therethrough.

18. A method for delivering fluid to a persons' teeth and mouth using a powered dental cleaning device comprising:

a) providing a fluid delivery dental cleaning device having a handle having drive means therein, a mounting end having a drive coupling, a removable neck having a complementary mounting end and a mating drive coupling for attaching to the drive coupling on the handle, a tool mounting receptacle located at an end of the neck, a fluid reservoir composed of a resilient material incorporated in the neck, fluid delivery means in fluid communication with the fluid reservoir and with the tool mounting receptacle for supplying fluid thereto;

b) providing fluid in the fluid reservoir;

c) delivering fluid to a tool mounted in the tool mounting receptacle; and, d) applying the fluid to the teeth and mouth while using the tool.

19. The method of claim 18 wherein the fluid is selected from the group consisting of medicaments, dentifrice, and mouthwash.

20. The method of claim 18 further comprising removing the neck from the handle and placing a second neck on the handle, the second neck having a fluid reservoir containing a different fluid; and, repeating steps c and d.

21. The method of claim 18 further comprising selecting a tool from the group consisting of a brush, a nozzle and a tongue scraper and mounting the tool in the tool receiving receptacle.

22. The method of claim 21 wherein the tool is a brush and the fluid is applied while brushing the teeth.

23. The method of claim 21 wherein the tool is a nozzle and the fluid is applied prior to or after brushing the teeth.

24. The method of claim 21 wherein the tool is a tongue scraper and the fluid is applied during tongue scraping.

25. A dental cleaning device comprising a handle having drive means therein, a mounting end having a drive coupling, a removable neck having a complementary mounting end and a mating drive coupling for attaching to the drive coupling on the handle, a tool mounting receptacle located at an end of the neck, a fluid reservoir incorporated in the neck, fluid delivery means in fluid communication with the reservoir and with the tool mounting receptacle for supplying a fluid thereto, the neck being separable into two sections, a reservoir section and a separable drive neck section, the reservoir section housing the fluid reservoir and fluid delivery means, a reservoir drive coupling provided on a forward end thereof, the drive neck having the tool mounting receptacle and a complimentary drive coupling for attaching to the reservoir section.

26. The dental cleaning device of claim 25 wherein the fluid delivery means is a diaphragm pump.

27. The dental cleaning device of claim 26 wherein a diaphragm portion of the diaphragm pump is accessed through an opening in the neck for activation by finger pressure.

28. The dental cleaning device of claim 25 wherein the fluid reservoir has an entry port for placing fluid therein.

29. The dental cleaning device of claim 25 further comprising a cam mounted on a drive shaft extending from the drive coupling through the neck, the cam in contact with the fluid delivery means for effecting a pumping action during rotation of the drive shaft.

30. The dental cleaning device of claim 25 wherein the tool mounting receptacle has a fluid receiving chamber adjacent a base of a tool mounted therein.

31. The dental cleaning device of claim 25 further comprising a distribution ring located around the tool mounting receptacle.

32. The dental cleaning device of claim 25 wherein the fluid delivery means is a pump/motor, a switch for activating the pump/motor located on the removable neck.

33. The dental cleaning device of claim 25 wherein the fluid reservoir is concentric to the tool mounting receptacle.

34. The dental cleaning device of claim 25 further comprising a distribution ring located around the tool mounting receptacle.

35. The dental cleaning device of claim 25 further comprising a tool selected from the group consisting of a brush, a tongue scraper and a nozzle.

36. The dental cleaning device of claim 25 wherein a brush is mounted in the tool mounting receptacle.

37. The dental cleaning device of claim 36 wherein the brush has a base having grooves about an outside periphery thereof for passing fluid thereby.

38. The dental cleaning device of claim 36 wherein the brush has a base having holes therethrough.

39. The dental cleaning device of claim 36 wherein the brush has a tuft containing tubular fibers having open ends extending through a base of the brush for passing a fluid therethrough.

40. The dental cleaning device of claim 25 further comprising a tongue scraper mounted in the tool mounting receptacle, the tongue scraper having an edge, openings provided in the edge for delivering fluid therethrough.

41. A dental cleaning device dental cleaning device comprising a handle having drive means therein, a mounting and having a drive coupling, a removable neck having a complementary mounting and a mating drive coupling for attaching to the drive coupling on the handle, a tool mounting receptacle located at an end of the neck, a fluid reservoir incorporated in the neck, a fluid delivery means in fluid communication with the reservoir and with the tool mounting receptacle for supplying a fluid thereto; the fluid delivery means being a diaphragm pump.

42. The dental cleaning device of claim 41 wherein the neck being separable into two sections, a reservoir section and a separable drive neck section, the reservoir section housing the fluid reservoir and fluid delivery means, a reservoir drive coupling provided on a forward end thereof, the drive neck having the tool mounting receptacle and a complimentary drive coupling for attaching to the reservoir section.

43. The dental cleaning device of claim 41 wherein the fluid reservoir has an entry port for placing fluid therein.

44. The dental cleaning device of claim 41 further comprising a cam mounted on a drive shaft extending from the drive coupling through the neck, the cam in contact with the diaphragm pump for effecting a pumping action during rotation of the drive shaft.

45. The dental cleaning device dental cleaning device of claim 41 wherein a diaphragm portion of the diaphragm pump is accessed through an opening in the neck for activation by finger pressure.

46. The dental cleaning device of claim 41 wherein the tool mounting receptacle has a fluid receiving chamber adjacent a base of a tool mounted therein.

47. The dental cleaning device of claim 41 further comprising a distribution ring located around the tool mounting receptacle.

48. The dental cleaning device of claim 41 wherein the fluid delivery means is a pump/motor, a switch for activating the pump/motor located on the removable neck.

49. The dental cleaning device of claim 41 wherein the fluid reservoir is concentric to the tool mounting receptacle.

50. The dental cleaning device of claim 41 further comprising a distribution ring located around the tool mounting receptacle.

51. The dental cleaning device of claim 41 further comprising a tool selected from the group consisting of a brush, a tongue scraper and a nozzle.

52. The dental cleaning device of claim 41 wherein a brush is mounted in the tool mounting receptacle.

53. The dental cleaning device of claim 52 wherein the brush has a base having grooves about an outside periphery thereof for passing fluid thereby.

54. The dental cleaning device of claim 52 wherein the brush has a base having holes therethrough.

55. The dental cleaning device of claim 52 wherein the brush has a tuft containing tubular fibers having open ends extending through a base of the brush for passing a fluid therethrough.

56. The dental cleaning device of claim 52 further comprising a tongue scraper mounted in the tool mounting receptacle, the tongue scraper having an edge, openings provided in the edge for delivering fluid therethrough.

57. A dental cleaning device comprising a handle having drive means therein, a mounting and having a drive coupling, a removable neck having a complementary mounting and a mating drive coupling for attaching to the drive coupling on the handle, a tool mounting receptacle located at an end of the neck, a fluid reservoir incorporated in the neck, a fluid delivery means in fluid communication with the reservoir and with the tool mounting receptacle for supplying a fluid thereto; a cam mounted on a drive shaft extending from the drive coupling through the neck, the cam in contact with the fluid delivery means for effecting a pumping action during rotation of the drive shaft.

58. The dental cleaning device of claim 57 wherein the fluid delivery means is a diaphragm pump.

59. The dental cleaning device of claim 58 wherein a diaphragm portion of the diaphragm pump is accessed through an opening in the neck for activation by finger pressure.

60. The dental cleaning device of claim 57 wherein the fluid reservoir has an entry port for placing fluid therein.

61. The dental cleaning device of claim 57 wherein the tool mounting receptacle has a fluid receiving chamber adjacent a base of a tool mounted therein.

62. The dental cleaning device of claim 57 further comprising a distribution ring located around the tool mounting receptacle.

63. The dental cleaning device of claim 57 wherein the fluid delivery means is a pump/motor, a switch for activating the pump/motor located on the removable neck.

64. The dental cleaning device of claims wherein the fluid reservoir is concentric to the tool mounting receptacle.

65. The dental cleaning device of claim 57 further comprising a distribution ring located around the tool mounting receptacle.

66. The dental cleaning device of claim 57 further comprising a tool selected from the group consisting of a brush, a tongue scraper and a nozzle.

67. The dental cleaning device of claim 57 wherein a brush is mounted in the tool mounting receptacle.

68. The dental cleaning device of claim 67 wherein the brush has a base having grooves about an outside periphery thereof for passing fluid thereby.

69. The dental cleaning device of claim 67 wherein the brush has a base having holes therethrough.

70. The dental cleaning device of claim 67 wherein the brush has a tuft containing tubular fibers having open ends extending through a base of the brush for passing a fluid therethrough.

71. The dental cleaning device of claim 57 further comprising a tongue scraper mounted in the tool mounting receptacle, the tongue scraper having an edge, openings provided in the edge for delivering fluid therethrough.

72. A dental cleaning device comprising a handle having drive means therein, a mounting and having a drive coupling, a removable neck having a complementary mounting and a mating drive coupling for attaching to the drive coupling on the handle, a tool mounting receptacle located at an end of the neck, a fluid reservoir incorporated in the neck, a fluid delivery means in fluid communication with the reservoir and with the tool mounting receptacle for supplying a fluid thereto; insert the fluid delivery means being a pump/motor, a switch for activating the pump/motor located on the removable neck.

73. The dental cleaning device of claim 72 wherein the fluid delivery means is a diaphragm pump.

74. The dental cleaning device of claim 73 wherein a diaphragm portion of the diaphragm pump is accessed through an opening in the neck for activation by finger pressure.

75. The dental cleaning device of claim 72 wherein the fluid reservoir has an entry port for placing fluid therein.

76. The dental cleaning device of claim 72 further comprising a cam mounted on a drive shaft extending from the drive coupling through the neck, the cam in contact with the fluid delivery means for effecting a pumping action during rotation of the drive shaft.

77. The dental cleaning device of claim 72 wherein the tool mounting receptacle has a fluid receiving chamber adjacent a base of a tool mounted therein.

78. The dental cleaning device of claim 72 further comprising a distribution ring located around the tool mounting receptacle.

79. The dental cleaning device of claim 72 wherein the fluid reservoir is concentric to the tool mounting receptacle.

80. The dental cleaning device of claim 72 further comprising a distribution ring located around the tool mounting receptacle.

81. The dental cleaning device of claim 72 further comprising a tool selected from the group consisting of a brush, a tongue scraper and a nozzle.

82. The dental cleaning device of claim 72 wherein a brush is mounted in the tool mounting receptacle.

83. The dental cleaning device of claim 82 wherein the brush has a base having grooves about an outside periphery thereof for passing fluid thereby.

84. The dental cleaning device of claim 82 wherein the brush has a base having holes therethrough.

85. The dental cleaning device of claim 82 wherein the brush has a tuft containing tubular fibers having open ends extending through a base of the brush for passing a fluid therethrough.

86. The dental cleaning device of claim 72 further comprising a tongue scraper mounted in the tool mounting receptacle, the tongue scraper having an edge, openings provided in the edge for delivering fluid therethrough.

* * * * *